United States Patent [19]

Hani et al.

[11] Patent Number: 5,929,132
[45] Date of Patent: *Jul. 27, 1999

[54] PROCESS FOR INCORPORATING BIOCIDES INTO A LIQUID DISPERSION

[75] Inventors: Rahim Hani; Cynthia M. Ward, both of Cheshire, Conn.

[73] Assignee: Arch Chemicals, Inc., Cheshire, Conn.

[ * ] Notice: This patent is subject to a terminal disclaimer.

[21] Appl. No.: 07/978,531

[22] Filed: Nov. 19, 1992

[51] Int. Cl.⁶ ...................................................... C08K 5/12
[52] U.S. Cl. ............................................................ 523/122
[58] Field of Search ........................... 523/122; 524/178, 524/179, 176, 175, 296, 297; 424/406, 407, 419, 78.03, 78.02, 907

[56] References Cited

U.S. PATENT DOCUMENTS

| | | | |
|---|---|---|---|
| 3,911,135 | 10/1975 | Tirpak | 523/122 |
| 4,086,297 | 4/1978 | Rei et al. | 523/122 |
| 4,661,528 | 4/1987 | Rei | 523/122 |
| 4,663,359 | 5/1987 | Rei | 523/122 |
| 4,678,684 | 7/1987 | Sand | 523/122 |
| 4,683,080 | 7/1987 | Rei et al. | 523/122 |
| 5,102,657 | 4/1992 | Rei et al. | 523/122 |
| 5,319,000 | 6/1994 | O'Connor et al. | |
| 5,639,803 | 6/1997 | Anderson et al. | |

FOREIGN PATENT DOCUMENTS 835936  3/1970  Canada.

*Primary Examiner*—Veronica P. Hoke
*Attorney, Agent, or Firm*—Dale Lynn Carlson; Todd E. Garabedian; Wiggin & Dana

[57] ABSTRACT

This invention relates to a process improvement for preparing a storage-stable dispersion of a biocide which comprises the steps of: (a) dispersing a solid biocide and a carrier to form a biocide concentrate, (b) heating said biocide concentrate to an elevated temperature to provide a storage stable mixture of biocide, resin and carrier, and (c) cooling said mixture under continuous stirring to provide a homogeneous, storage-stable liquid dispersion. Also claimed is the storage-stable product produced by this process.

9 Claims, No Drawings

PROCESS FOR INCORPORATING BIOCIDES INTO A LIQUID DISPERSION

FIELD OF THE INVENTION

The present invention relates generally to an improved delivery system for polymer additives, and, more specifically, to a process for providing physically stable dispersions of a biocide in a polymer resin composition.

BACKGROUND OF THE INVENTION

Various methods for incorporating biocides into resin compositions have been disclosed in the prior art. By way of illustration, U.S. Pat. No. 4,086,297 discloses a process for forming a solid thermoplastic composition containing a microbiocide utilizing very high levels of the microbiocide and two thermoplastic resins in conjunction with melt blending processing.

As another illustration, U.S. Pat. No. 4,663,359 discloses a process for preparing a microbiocide concentrate which is useful in plastisol systems. The process comprises mixing a porous thermoplastic resin powder with a high concentration of microbiocide at an elevated temperature sufficient to melt the biocide and open the pores of the resin, and incorporating the melted biocide into the pores of the porous resin, optionally in the presence of a carrier. The resulting product is provided as a dry, free-flowing powder containing the microbiocide in a high concentration at least about 20 times greater than the normal upper usage concentration for the microbiocide.

Unfortunately, the products produced in accordance with the above-mentioned '297 and '359 patents are solids which are frequently more difficult to process into a finished product than might be desired. Biocide dispersions (i.e., solid particles dispersed in a liquid) would avoid such solids handling problems in subsequent processing steps. Heretofore, however, suitable methods for incorporating insoluble or difficult-to-solubilize biocides into plastics to form dispersions has represented a challenge to the plastics manufacturing community. The solids in such dispersions tend to settle out over time, thus causing a non-uniform distribution of the additive in the dispersion. In addition, certain dispersions, most notably plastisols, have the tendency to increase in viscosity with increasing temperature, thus posing a risk that the dispersion will "set-up" or solidify during storage and/or handling prior to use.

One more successful effort to provide a biocide-containing dispersion is disclosed in U.S. Pat. No. 5,639,803. Briefly, this patent discloses a multi-step process comprising (a) forming an aqueous concentrate of biocide, carrier and water, (b) heating the concentrate to remove the water and (c) adding additional carrier and a heat swellable polymer to form a storage-stable dispersion of the biocide in the polymer. Example 1 of this patent application teaches heating in step (b) above to a temperature of 91° C. and driving off the water. Unfortunately, it has now been found by the present inventors that this heating step causes undesirable discoloration of the concentrate, and this discoloration remains present in the final dispersion.

In view of the above, new methods for incorporating insoluble or difficult-to-solubilize biocides into plastics resins that avoid the settling, discoloration and/or viscosity increase problems of the prior art compositions would be highly desired by the plastics manufacturing community.

SUMMARY OF THE INVENTION

The present invention relates to a process for preparing a storage-stable dispersion of a biocide which comprises the steps of:

(a) forming a biocide/carrier concentrate containing 1 to 70 percent biocide (preferably 20 to 50 percent biocide) by mixing a solid biocide and a liquid carrier (preferably in a high speed mixer and more preferably at a speed of 3500 to 7000 revolutions per minute) until a desired particle size for said biocide is obtained;

(b) heating said mixture of biocide concentrate and a heat swellable polymer to an elevated temperature of between about 50° C. and about 120° C. (preferably between about 70° C. and about 110° C.) to cause said polymer to swell by carrier absorption into said polymer, thereby providing a swelled polymer plus biocide mixture in said carrier characterized by an increased viscosity sufficient to provide a hot dispersion; and (c) cooling said hot dispersion under continuous stirring to a temperature of between about −20° C. and about 40° C. to provide a storage-stable mixture having a viscosity of between about 2,000 and about 30,000 (preferably between about 5,000 and about 15,000) centipoise.

The present invention relates to the storage-stable compositions produced by above processes. This aspect and others will become apparent upon reading the following detailed description of the invention.

DETAILED DESCRIPTION OF THE INVENTION

In accordance with the present invention, it has now been surprisingly found that storage-stable dispersions of solid biocides in swellable polymer resins are provided by causing carrier absorption into the polymer to occur under elevated temperature conditions. The resulting dispersions are storage-stable against settling and against "setting-up" that would otherwise typically occur during warehousing of the dispersions prior to use.

Carriers useful in the process of the present invention include, for example, plasticizers and other resin-compatible additives. Useful plasticizer-type carriers include, for example, adipic acid derivatives such as diisobutyl adipate, di-n-hexyl adipate, heptyl nonyl adipate, bis(2-ethylhexyl) adipate, diisodecyl adipate and bis(2-butoxyethyl)adipate; azelaic acid derivatives such as bis(2-ethylhexyl)azelate; benzoic acid derivatives such as diethylene glycol dibenzoate, dipropyleneglycol dibenzoate, and 2,2,4-trimethyl-1, 3-pentanediol-isobutyrate benzoate; citric acid derivatives such as tri-n-butyl citrate and tri-n-butyl acetylcitrate; epoxy derivatives such as epoxidized soybean oil, epoxidized linseed oil, 2-ethylhexyl epoxy tallate and bisphenol A diglycidyl ether; glycol derivatives such as diethlyene glycol dipelargonate, triethylene glycol di-2-ethylbutyrate, and poly(ethylene glycol) (200) di-2-ethylhexanoate; glycolates such as methyl phthalyl ethyl glycolate and butylphthalyl ethyl glycolate; hydrocarbons such as hydrogenated terphenyls HB-40, poly(alkyl naphthalenes) Panaflex, aliphatic aromatics [LEROMOLL] and chlorinated paraffin (52% wt % C1) [CERECLOR S-52]; isophthalic acid derivatives such as di-2-ethylhexyl isophthalate; oleic acid derivatives such as butyl oleate; phosphoric acid derivatives such as tributyl phosphate, tri-2-ethylhexyl phosphate, tributoxyethyl phosphate, chlorinated diphosphate (PHOSGARD 2XC-20], cresyl diphenyl phosphate, tricresyl phosphate, isopropylphenyl diphenyl phosphate [KROTINEX 100], t-butylphenyl diphenyl phosphate [SANTICIZER 154], 2-ethylhexyl diphenyl phosphate and isodecyl phosphate; phosphoric acid derivatives such as chlorinated polyphosphonate [PHOSGARD C-22-R]; phthalic acid derivatives such as dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$–$C_{11}$) mixed linear phthalates [SANTICIZER 711 or PLATINOL 711P], bis(2-ethylhexyl)phthalate, (n-hexyl, n-octyl, n-decyl) phthalate, (n-octyl, n-decyl)phthalate, diisodecyl phthalate, diundecyl phthalate, ditridecylphthalate, butyl cyclohexyl phthalate, butyl benzyl phthalate, diisononyl phthalate, 7-(2,6,6,8-tetramethyl-4-oxa-3-oxo-nonyl)benzyl phthalate, bis (2-butoxyethyl)phthalate and dicylclohexyl phthalate; polyesters such as adipic acid polyester (mol wt 6000) [PARAPLEX G-40], adipic acid polyester (mol wt 2000) [SANTICIZER 334F], azelaic acid polyester (mol wt 850) [PLASTOLEIN 9720], azelaic acid polyester (mol wt 2200) [PLASTOLEIN 9750] and sebacic acid polyester; ricinoleic acid derivatives such as methyl ricinoleate, n-butyl acetylricinoleate and castor oil (90 wt % glyceryl ricinoleate); sebacic acid derivatives such as bis(2-ethylhexyl)sebacate; stearic acid derivatives such as butyl acetoxystearate; sucrose derivatives such as sucrose acetate-isobutyrate; sulfonic acid derivatives such as N-thyl-(o,p)-toluenesulfonamide and alkylsulfonic acid ester of phenol and cresol [MESAMOLL]; terephthalic acid derivatives such as bis(2-ethylhexyl)terephthalate; and trimellitic acid derivatives such as tris(2-ethylhexyl)trimellitate, heptyl nonyl trimellitate, heptyl nonyl undecyl trimellitate and triisodecyl trimellitate.

Other useful carriers include additives not normally classified as plasticizers, such as polyols. An important criterion for the additive(s) useful as carriers within the scope of the present invention is that the additive(s) interacts with the selected swellable polymer resin upon heating to cause swelling of the polymer particles. In order for the carrier to be useful in a specific application, swelling of the polymer particles must occur at an elevated temperature below the degradation temperature of the polymer and of the carrier. Heat stabilizers can optionally be employed in order to avoid elevated degradation temperatures.

The amount of carrier employed in the processes of the present invention suitably ranges between about 20 and about 95, preferably between about 50 and about 85, weight percent based upon the total weight of the dispersion.

Suitable heat swellable polymer resins useful in the present invention include, for example, the following resins and combinations thereof: cellulosics such as cellulose acetate, cellulose acetate-butyrate, cellulose nitrate, and ethylcellulose; polyacrylates such as poly(methyl methacrylate) and acrylic copolymers, polystyrenes; polyolefins such as polyethylene and polypropylene; polycarbonates; rubbers and synthetic elastomers; vinyl polymers such as polyvinyl acetate), poly(vinyl butyral), poly(vinyl alcohol) and poly(vinylchloride); and polyacrylonitrile and modified copolymers thereof; and combinations thereof. The degree of crystallinity of any particular polymer may affect the extent of carrier absorption into the polymer for the specific carrier selected, as would be readily apparent to those of ordinary skill in the art.

The amount of swellable polymer resin(s) employed in the processes of the present invention suitably ranges between about 1 and about 60, preferably between about 5 and about 40, weight percent based upon the total weight of the dispersion.

Suitable biocides useful in the present invention include, for example, the following biocides and combinations thereof:

OBPA—10,10'-oxybisphenoxarsine
VANCIDE 89—N-(trichloromethylthio)-4-cyclohexene-1, 2-dicarboximide
DOWCIL A-40-2,3,5-trichloro-4-propylsulfonyl pyridine
zinc OMADINE®—zinc salt of 1-hydroxypyridine-2-thione
sodium OMADINE—sodium salt of 1-hydroxypyridine-2-thione
OMADINE® MDS—the magnesium salt of pyrithione disulfide
Copper pyrithione
Pyrithione disulfide
chitosan OMADINE—chitosan pyrithione
FUNGITROL 11—N-(trichloromethylthio)phthalimide
N-(2-methylnaphthyl)maleimide
DIFOLATAN—cis-N-(1,1,2,2-tetrachloroethyl)-thio-4-cyclohexene-1,2-dicarboximide
ISOLAN—1-isopropyl-3-methyl pyrazolyl-5-dimethyl carbamate 3-methyl-pyrazolyl dimethylcarbamate
MANEB—manganese ethylene bisdithiocarbamate
ZINEB—zinc analog of Maneb
NABAM—disodium analog of Maneb
FERBAM—ferric dimethyl dithiocarbamate
ZIRAM—zinc analog of Ferbam
XARATHANE—2,4-dinitro-6-capryl phenol crotonate
OVATRAN—p-chlorophenyl-p-chlorobenzenesulphonate
SKANE M-8—2-N-octyl-4-isothiazolin-3-one
Benomyl-methyl-1(butylcarbamoyl)-2-benzimidazole carbamate
METASOL TK-100—2(4-thiazolyl)benzimidazole
Copper-8—copper 8-hydroxy-quinolinate
a-diethoxyphosphinodithioacetylurea
a-dimethoxyphosphinodithioacetylurea
Diethoxyphosphinodithioacetamide
Dimethoxyphosphinodirhioacetamide
Bis(dimethylamido)phosphoryl fluoride
Tributyl tin fluoride
2-cyclohexyl-3-isothiazolone
4,5-dichloro-2-cyclohexyl-3-isothiazolone The above biocides are suitably employed individually or in combinations of two or more biocides, as may be desired. The preferred biocides are sodium pyrithione, zinc pyrithione, copper pyrithione, chitosan pyrithione, pyrithione disulfide, and combinations thereof.

The biocide(s) is typically employed in an amount of between about one and about 50, preferably between about 5 and about 30, weight percent based upon the total weight of the dispersion. The processes of the present invention are suitable for the preparation of resin concentrates, if desired, containing high levels of biocide. The concentrates are subsequently diluted with additional polymer resin, which can be the same or different resin from that used in the preparation of the concentrate, to provide a working composition containing at least a "biocidally effective amount" of biocide, i.e., an amount of biocide sufficient to provide the desired level of biocidal efficacy in the working composition. Selection of the carrier for use in the preparation of a concentrate advantageously takes into account additives that are desirably present in the working composition. Alternatively, the working composition is suitably prepared directly using the processes of the present invention without the necessity for preparing a concentrate. The processes of the present invention are suitably effected in a few minutes or less up to ten hours or more, depending upon the specific starting materials and processing conditions employed.

Other additives are suitably optionally employed in the processes of the present invention, including for example pigments such as titanium dioxide, fillers and reinforcing agents such as glass fibers, heat stabilizers such as calcium sterate, uv stabilizers, surfactants such as polyalkyleneoxide ethers, dispersing agents, suspending agents, and the like, and combinations thereof. If used, the optional additives are suitably employed in a minor amount of less than fifty weight percent based upon the weight of the polymer resin.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

Part A—Preparation of a Preliminary Zinc Pyrithione/Plasticizer Dispersion Referred to Herein as ("the concentrate")

Dioctyl phthalate (DOP) (1000 grams) was added to zinc pyrithione powder (600 grams) in a steel beaker and mixed on a high speed disperser at 6000 rpm until smooth (approx. two hours). The concentrate temperature did not exceed 100° C.

Part B—Preparation of a 5% Zinc Pyrithione Dispersion Containing 20% PVC Prepared at an Elevated Temperature Zinc pyrithione dispersion (110.9 grams; 37.5% active in DOP), prepared in accordance with Part A above, was combined with BF Goodrich GEON 125A PVC (160.0 grams) and DOP (529.1 grams). Stirring was continued throughout the reaction. The mixture was warmed to 80° C. using an oil bath. The temperature was maintained for 3.5 hours. The heat was removed, the mixture was allowed to air cool overnight to room temperature with continued stirring. The resulting dispersion containing 5% zinc pyrithione and 20% PVC was stable at room temperature and had a static viscosity of approx. 6,400 cps at 25° C.

EXAMPLE 2

Part A—Preparation of a Preliminary Zinc Pyrithione/Plasticizer Dispersion

Epoxidized soybean oil (ESO) (406 grams) was added to dry zinc pyrithione powder (200 grams) in a stainless steel beaker and mixed on a high speed disperser at 3500 rpm for 2 hours.

Part B—Preparation of a 5% Zinc Pyrithione Dispersion Containing 23% PVC Prepared at an Elevated Temperature Zinc pyrithione dispersion (100.7 grams; 31% active in ESO) prepared in accordance with part A above, was combined with BF Goodrich GEON 125A PVC (138 grams) and ESO (361.4 grams). Stirring was continued throughout the reaction. The mixture was warmed to 80° C. using an oil bath. The temperature was maintained for 4 hours. The heat was removed, and the mixture was allowed to air cool with continued stirring until it reached room temperature. The resulting dispersion containing 5% zinc pyrithione and 23% PVC was stable at room temperature and had a viscosity of 13000 centipoise at 23° C. with stirring.

EXAMPLE 3

Heating Effect on the Viscosity of a 5% Zinc Pyrithione Dispersion Containing 28.5% PVC A dispersion was prepared following the procedure of Example 1 by combining zinc pyrithione preliminary dispersion (111.2 grams; 37.4% active in 711) with BF Goodrich GEON 125A Plastisol grade PVC and 711.

Stirring was continued throughout the reaction. The mixture was warmed to 80° C. using an oil bath. Aliquots of the sample were taken at half hour intervals to follow the sample's viscosity profile. The dispersion viscosity was found to increase with time for 2.5 hours, and then the viscosity became constant.

| Time (hours) | Viscosity (cps) |
|---|---|
| 0 | 3410 |
| 0.5 | 5010 |
| 1.0 | 6800 |
| 1.5 | 7210 |
| 2.0 | 7400 |
| 2.5 | 9520 |
| 3.0 | 9600 |
| 3.5 | 9520 |

Viscosity was found to be a direct function of temperature and polymer concentration.

EXAMPLE 4

Preparation of 5% Zinc Pyrithione Dispersions in a Dioctyl Phthalate Carrier

A series of dispersions were prepared following the procedure of Example 1 by combining zinc pyrithione preliminary dispersion (35% active in DOP [Dioctyl Phthalate]) with BF Goodrich GEON 125A Plastisol grade PVC and DOP. These formulations were heated using an oil bath and varying amounts of PVC for 4 hours. The amounts of pyrithione concentrate (35% active), PVC and DOP for each formulation are as follows:

| Formulation | (grams) | PVC | DOP |
|---|---|---|---|
| Sample a | 89.14 | 120 | 390.89 |
| Sample b | 89.14 | 126 | 384.86 |
| Sample c | 89.14 | 123 | 387.86 |
| Sample d | 89.14 | 108 | 402.86 |

All dispersions identified as Samples a, b, c, and d were found to have acceptable viscosities ranging from 6,000–15,000 cps. As expected, higher polymer levels produced more viscous materials.

EXAMPLE 5

20% Pyrithione Dispersion in Epoxidized Soybean Oil (ESO) Carrier

A dispersion was prepared following the procedure of Example 1 by combining zinc pyrithione preliminary dispersion (266.67 grams; 30% active in ESO) with 48 grams BF Goodrich GEON 125A Plastisol grade PVC and 85.33 grams ESO. This formulation was heated, using an oil bath, to 80° C. for four hours. The sample was found to have an acceptable viscosity of approx. 7,000 cps.

EXAMPLE 6

5% Pyrithione Dispersion in Butly Benzyl Phthalate (BBP) Carrier

A series of dispersions were prepared following the procedure of Example 1 by combining zinc pyrithione preliminary dispersion (96.36 grams; 30% active in (BBP) with BF Goodrich GEON 125A Plastisol grade PVC and BBP. These formulations were heated, using an oil bath, to 80° C. for 4 hours. The formulations had an acceptable viscosity range from 9,000 to 13,000 cps.

EXAMPLE 7

5% Zinc Pyrithione Dispersion in Diisodecyl Phthalate (DIDP) Carrier

A series of dispersions were prepared following the procedure of Example 1 by combining zinc pyrithione preliminary dispersion (100.65 grams; 31% active in DIDP) with BF Goodrich GEON 125A Plastisol grade PVC and DIDP. Stirring was continued throughout the reaction. The mixture was warmed to 80° C. for four hours using an oil bath.

All the samples had acceptable viscosities ranging from 7,000 to 10,000 cps and were stable dispersions.

EXAMPLE 8

Stability of a 5% Zinc Pyrithione Dispersion in BBP Containing 15% PVC

A dispersion was prepared following the procedure of example 1 by combining zinc pyrithione preliminary dispersion (96.36 grams; 33% active in BBP) with BF Goodrich GEON 125A Plastisol grade PVC and BBP. The dispersion was heated using an oil bath to 80° C. for four hours.

This dispersion had an acceptable viscosity of 12,000 cps. The amount of zinc was measured at the top and bottom of this sample by x-ray fluorescence to ensure a stable dispersion with no settling. Sample A, which was at room temperature for 3 months, had zinc measurements of 0.60 and 0.60 at the bottom and top of the sample, respectively. Sample B, which was stored at an elevated temperature of 50° C. for 3 months had zinc values of 0.60 and 0.60 at the bottom and top of the sample, respectively. These measurements show that the sample is a storage stable dispersion, even at elevated temperatures, and that settling does not occur.

EXAMPLE 9

Color Determination of Dispersion Made By New Method vs. Old Method

A dispersion was prepared following the procedure of Example 1 by combining zinc pyrithione preliminary dispersion with Gooodrich GEON 125A Plastisol grade PVC and DOP. The sample was found to have a "b" value on a Hunter Colorimeter of 7.56. This value measures yellowness.

The previous method (i.e., the method of U.S. Pat. No. 5,639,803) used to make a similar formulation entails mixing zinc pyrithione wet cake (20% water) and a carrier. This mixture is then heated to an elevated temperature, to remove the water, while stirring for approx. 4 hours. Mixing together said concentrate, additional carrier and Goodrich GEON 125A Plastisol grade PVC, the mixture is then prepared similarly to part B of example 1 above.

A sample of the material prepared in the previous manner, containing the water removal step, was measured using the Hunter Colorimeter. This sample's "b" value was measured at 19.56. This second sample (i.e., the comparative example) has almost twice the amount of yellowing as the first sample measured.

What is claimed is:

1. A process for preparing a storage stable dispersion of a solid biocide which comprises the steps of:

(a) forming, in the absence of water, a biocide/carrier concentrate containing 1 to 70 percent biocide by mixing a solid biocide and a liquid carrier until a desired particle size for said biocide is obtained;

(b) heating, in the absence of water, a mixture of said biocide/carrier concentrate and a heat swellable polymer to an elevated temperature of between about 50° C. and about 120° C. to cause said polymer to swell by carrier absorption into said polymer, thereby providing a swelled polymer plus biocide mixture in said carrier characterized by an increased viscosity sufficient to provide a hot dispersion; and (c) cooling said hot dispersion under continuous stirring to a temperature of between about −20° C. and about 40° C. to provide a storage-stable dispersion having a viscosity of between 2,000 and 30,000 centipoise.

2. The process of claim 1 wherein said biocide is selected from the group consisting of sodium pyrithione, zinc pyrithione, chitosan pyrithione, and combinations thereof.

3. The process of claim 1 wherein said biocide is employed in an amount of between about 1 and about 50 weight percent based upon the total weight of the dispersion.

4. The process of claim 1 wherein said carrier is selected from the group consisting of dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$–$C_{11}$) mixed linear phthalates, bis(2-ethylhexyl)phthalate, (n-hexyl, n-octyl, n-decyl)phthalate, (n-octyl, n-decyl)phthalate, diisodecyl phthalate, diundecyl phthalate, ditridecylphthalate, butyl cyclohexyl phthalate, butyl benzyl phthalate, diisononyl phthalate, 7-(2,6,6,8-tetramethyl-4-oxa-3-oxo-nonyl)benzyl phthalate, bis(2-butoxyethyl)phthalate, dicylclohexyl phthalate, epoxidized soybean oil, and combinations thereof.

5. The process of claim 1 wherein said carrier is employed in an amount of between about 20 and about 95 weight percent based upon the total weight of the dispersion.

6. The process of claim 1 wherein the biocide is employed in an amount of between 1 and 60 weight percent based upon the total weight of the dispersion.

7. The process of claim 1 wherein said heat-swellable polymer is polyvinyl chloride.

8. The process of claim 1 wherein said heat-swellable polymer is selected from the group consisting of poly(vinyl acetate), poly(vinyl butyral), poly(vinyl alcohol), poly (vinylchloride), and combinations thereof.

9. The process of claim 1 wherein said mixing of step (a) is carried out using a high speed mixer at a mixing speed of 3500 to 7000 revolutions per minute.

\* \* \* \* \*